US008830476B2

(12) United States Patent
Berg et al.

(10) Patent No.: US 8,830,476 B2
(45) Date of Patent: Sep. 9, 2014

(54) METHODS AND APPARATUSES FOR CONTACT-FREE HOLOGRAPHIC IMAGING OF AEROSOL PARTICLES

(75) Inventors: Matthew J. Berg, Mississippi State, MS (US); Gorden Videen, Adelphi, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 75 days.

(21) Appl. No.: 13/423,825

(22) Filed: Mar. 19, 2012

(65) Prior Publication Data
US 2013/0242301 A1    Sep. 19, 2013

(51) Int. Cl.
*G01B 9/021*  (2006.01)
*G01N 15/02*  (2006.01)
(52) U.S. Cl.
CPC .................................. *G01N 15/0227* (2013.01)
USPC .......................................................... 356/458
(58) Field of Classification Search
CPC ... G03H 1/0406; G03H 1/0443; G01N 15/02; G01N 15/0205; G01N 15/0227
USPC ......... 356/457, 458, 479, 497, 489, 495, 511, 356/512, 520, 477, 478, 480
See application file for complete search history.

(56) References Cited

U.S. PATENT DOCUMENTS

| | | | |
|---|---|---|---|
| 5,617,207 A * | 4/1997 | Glass et al. .................... | 356/477 |
| 6,411,406 B1 | 6/2002 | Kreuzer | |
| 6,573,997 B1 * | 6/2003 | Goldberg et al. ............. | 356/521 |
| 7,599,069 B2 * | 10/2009 | Toussaint et al. ............. | 356/491 |
| 2005/0261841 A1 * | 11/2005 | Shepard et al. ................ | 702/32 |

OTHER PUBLICATIONS

Christopher Mann, Lingfeng Yu, Chun-Min Lo, and Myung Kim, "High-resolution quantitative phase-contrast microscopy by digital holography," Opt. Express 13, 8693-8698 (2005).*
Lujie Cao, Gang Pan, Jeremy de Jong, Scott Woodward, and Hui Meng, "Hybrid digital holographic imaging system for three-dimensional dense particle field measurement," Appl. Opt. 47, 4501-4508 (2008).*
W. Xu, M. H. Jericho, I. A. Meinertzhagen, and H. J. Kreuzer, "Digital In-Line Holography of Microspheres," Appl. Opt. 41, 5367-5375 (2002).
M. Mishchenko, L. Travis, and A. Laois, "Multiple scattering of light by particles: radiative transfer and coherent backscattering," Cambridge: Cambridge University Press, 2006, pp. 74-78.

(Continued)

*Primary Examiner* — Michael A Lyons
*Assistant Examiner* — Willie Merrell, II
(74) *Attorney, Agent, or Firm* — Eric B. Compton

(57) ABSTRACT

Methods and apparatuses provide holographic contact-free imaging of aerosol particles in an efficient manner. One apparatus for holographic imaging of an aerosol particle may include: a delivery device configured to deliver the particle into a region; a light source for outputting a first beam of light and a second beam of light, wherein the first beam travels into the region producing a first light wave which is un-scattered by the particle and a second light wave that is scattered by the particle, and the second beam does not travel into the region; a beam splitter for combining the second beam with the scattered light of the first beam into combined interference light; an image sensor for sensing an interference pattern created by the combined interference light; and an image processor configured to generate an image of the aerosol particle based on the sensed interference pattern.

24 Claims, 7 Drawing Sheets

(56) References Cited

OTHER PUBLICATIONS

Aptowicz, K. B., R. G. Pinnick, S. C. Hill, Y. L. Pan, and R. K. Chang (2006), Optical scattering patterns from single urban aerosol particles at Adelphi, Maryland, USA: A classification relating to particle morphologies, J. Geophys. Res., 111, D12212.

Matthew J. Berg, Steven C. Hill, Gorden Videen, and Kristan P. Gurton, "Spatial filtering technique to image and measure two-dimensional near-forward scattering from single particles," Opt. Express 18, 9486-9495 (2010).

M. Berg and G. Videen, "Digital holographic imaging of aerosol particles in flight," Journal of Quantitative Spectroscopy & Radiative Transfer 112 (2011) pp. 1776-1783.

* cited by examiner

METHODS AND APPARATUSES FOR CONTACT-FREE HOLOGRAPHIC IMAGING OF AEROSOL PARTICLES

GOVERNMENT INTEREST

Governmental Interest—The invention described herein may be manufactured, used and licensed by or for the U.S. Government.

FIELD OF INVENTION

Embodiments of the present invention generally relate to particle imaging and, more particularly, to methods and apparatuses for contact-free holographic imaging of aerosol particles.

BACKGROUND OF THE INVENTION

The in situ characterization of small aerosol particles is a persistent objective in many applied contexts. Examples include the determination of atmospheric aerosol composition for climate modeling and the detection of biological or chemical weapons agents for defense applications. Various measurements and calculations of single and multiple-particle scattering patterns are known. The overall goal of such work is to infer information relating to the particles' physical form, such as size and shape, by analyzing the angular structure of these patterns. Unfortunately, a fundamental limitation of this approach is the absence of an unambiguous quantitative relationship between a pattern and the corresponding particle properties, i.e., the so-called inverse problem. Consequently, the inference of these properties from the patterns has proved to be very difficult in practice, except for the simplest of cases. Ideally, one would prefer to image the particles directly, thus eliminating the complexity and ambiguity associated with interpretation of the scattering patterns.

However, the typical particle size range of interest for many applications is roughly 0.1-10 µm. Because of the small size, direct images are possible in only part of this range and only with high numerical-aperture (NA) optics and small focal volumes. Such imaging typically requires the collection and immobilization of particle samples, and thus, is not a practical technique for particle characterization in applications requiring high sample through-put or images of the particles in their undisturbed form, i.e., in situ images.

Holography is an alternative technique that combines useful elements of both conventional imaging and scattering. Fundamentally, this is a two-step process: first, an object is illuminated with coherent light, and then the intensity pattern resulting from the interference of this light with that scattered by the particle is recorded. The resulting pattern constitutes the hologram, from which an image of the object is reconstructed. Traditionally, holograms are recorded with photographic film due to the film's high resolution. Such a high resolution medium is required to capture the finer features of the interference pattern. The subsequent chemical development of the film is costly and time consuming which greatly limits the practical utility of the technique.

BRIEF SUMMARY OF THE INVENTION

Methods and apparatuses for holographic contact-free imaging of aerosol particles in an efficient manner are described herein according to embodiments of the present invention.

According to one embodiment, an apparatus for holographic imaging of an aerosol particle may include: a delivery device configured to deliver the particle into a region; a light source for outputting a first beam of light and a second beam of light, wherein the first beam travels into the region producing a first light wave which is un-scattered by the particle and a second light wave that is scattered by the particle, and the second beam does not travel into the region; a beam splitter for combining the second beam with the scattered light of the first beam into combined interference light; an image sensor for sensing an interference pattern created by the combined interference light; and an image processor configured to generate an image of the aerosol particle based on the sensed interference pattern.

According to another embodiment, a method for holographic imaging of an aerosol particle may include: delivering the particle into a region; outputting a first beam of light and a second beam of light, wherein the first beam travels into the region producing a first light wave which is un-scattered by the particle and a second light wave that is scattered by the particle, and the second beam does not travel into the region; separating the scattered light from the un-scattered light of the first beam; combining the second beam with the scattered light of the first beam into combined interference light; sensing the interference pattern of the combined interference light; and generating an image of the aerosol particle based on the sensed interference pattern.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only a few embodiments of this invention and are therefore not to be considered limiting of its scope, for the invention may admit to other equally effective embodiments. These embodiments are intended to be included within the following description and protected by the accompanying claims.

DETAILED DESCRIPTION OF THE INVENTION

Embodiments of the present invention comprise forming a holographic image of particles using a light source to generate a wave which scatters when interacting with the aerosol particle and an un-scattered reference wave and recording the interference pattern between the scattering wave and the reference wave on an image sensor and using a computer-aided algorithm to generate an image from the interference pattern.

Aerosol particles of interest may include, for example, environmental hazards (e.g., asbestos, smog, smoke, etc.), chemicals, toxins, biological contaminants or spores (e.g., *E. coli* or anthrax), chemical or biological warfare agents, hydrosols (i.e., particles in water), other airborne contaminants (e.g., dust, pollen, or other pollutants), and the like. Particles may be already present in the air or originate in water, dirt, or other substances which may then become airborne.

The particle characterization techniques disclosed herein extend capabilities of elastic light scattering by using holography to form images of one or more particles, rather than their scattering patterns in embodiments. A particle's far-field scattering pattern interferes across the surface of an image sensor along with a reference wave having a portion of the light incident on the particle. For example, the scattered and reference wave may overlap in an in-line configuration embodiment and be separated, for instance, in an off-axis configuration, in other embodiments.

The resulting intensity distribution recorded by the image sensor is the particle's hologram. A three-dimensional image of the particle can then be generated computationally from the hologram. Further computational analysis of the resulting image can be performed to satisfy the requirements of the intended application, such as, for example, detection of particle size, shape, and/or other characteristics thereof. One advantage of these techniques is that there may be no further need to interpret or invert a complicated scattering pattern, as information can be retrieved directly from the image. Holography permits the reconstruction of phase, magnitude, or both, of the scattered wave pattern, for instance.

Using digital media, rather than traditional photographic film, holograms can be recorded rapidly in succession as the particles flow through the apparatus. This makes for a high "through-put" detection technique. Reconstructing images of a particle from its hologram digitally enables application of any number of image-analysis techniques intended to characterize the particle. For example, the digitally reconstructed particle-images can be automatically correlated with a library of simulated or measured images. This may enable a rapid detection/identification system.

Figure 1:
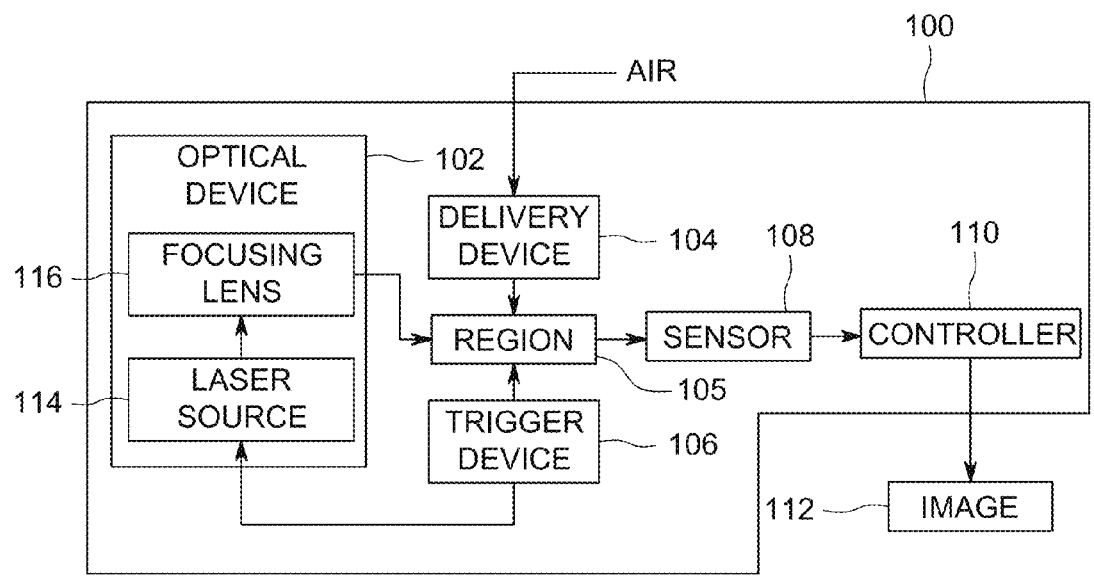
FIG. 1 is a functional block diagram of an inline apparatus for holographic imaging of aerosol particles in accordance with at least one embodiment of the present invention.

FIG. 1 is a functional block diagram of an inline apparatus for holographic imaging of aerosol particles in accordance with embodiments of the present invention. Apparatus 100 includes an optical device 102, a delivery device 104, a trigger device 106, an image sensor 108, and an image processor or controller 110. The optical device 102 comprises a laser light source 114 and a focusing lens 116. The delivery device 104 delivers particles into a region 105. In one embodiment, the particles are extracted from the air in the surrounding environment. In other embodiments, the particles are captured elsewhere and delivered to the delivery device for imaging. The trigger device 106 is actively detecting whether a particle has entered scattering volume region 105. When the trigger device 106 detects, as discussed below, that a particle has entered the region 105, a signal is sent to the optical device 102, indicating that the laser source 114 should be enabled. The optical device 102 may further enable the laser source 114 to pulse a laser into focusing lens 116. The focusing lens 116 creates a focused light wave that is directed at the region 105 where aerosol particles are detected, so that the particles scatter the focused light waves. In addition, the focusing lens 116 supplies light that is not scattered by the particles, and this light is incident on the sensor 108. The combination of the un-scattered and scattered light creates an interference pattern which is sensed by the sensor 108. The processor 110 executes a computer-implemented algorithm on the interference pattern, which constitutes the hologram, and generates an image 112 of the detected particles. In an embodiment, the computer-aided algorithm is a Fourier Transform and the Fourier transform is implemented computationally as a Fast Fourier Transform (FFT).

Figure 2:
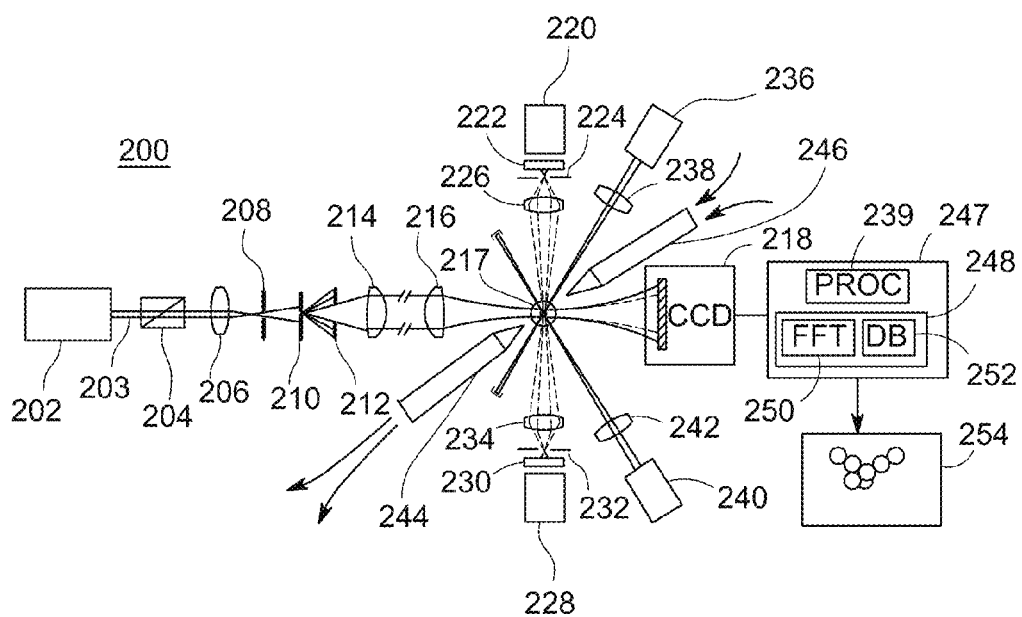
FIGS. 2 and 2(a)-2(e) are implementations of the inline apparatus of FIG. 1 in accordance with embodiments of the present invention.
Figure 2A:
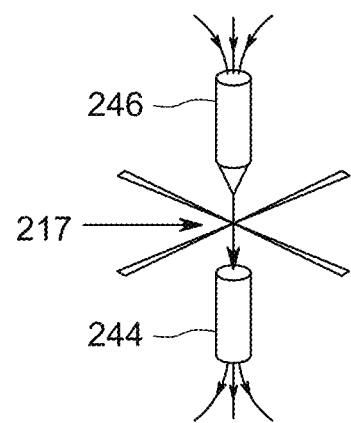

FIG. 2 is a schematic of an implementation 200 of apparatus 100 of FIG. 1 in accordance with embodiments of the present invention. Implementation 200 comprises a laser 202, a series of lenses and optics, 204, 206, 208, 210, 212, 214 and 216, an image sensor 218 (such as a CCD, shown), two photomultiplier tubes (PMT) 220 and 228, each with line filters 222 and 230, irises 224 and 232, lenses 226 and 234, and two diode lasers 236 and 240, each with convex lenses 238 and 242. In an embodiment, the laser 202 may be a 70 ns pulsed Nd:YAG laser (e.g., Spectra Physics Lasers, Inc., model Y70-532Q), frequency doubled to 532 nm. In an embodiment, implementation 200 is an "inline" configuration where all of the component parts 202-218 are configured in a line on a single plane. In other embodiments, the laser 202 may generate and output light that is ultraviolet (UV), visible, infrared (IR), or the like.

The optical device 102 in FIG. 1 may be implemented with the laser 202 and the optics 204-216. The laser 202 outputs a light wave 203 into a polarizer 204. The polarizer 204 polarizes the light 203. In an embodiment, the polarizer is a Glan-Thompson polarizer, though the present invention does not restrict the type of polarizer used. The light from the polarizer 204 is directed towards a convex lens 206 for focusing onto a pinhole 208, which, in an embodiment, the convex lens 206 has a focal length of 75 mm and the pinhole 208 has a 50 μm diameter. The primary lobe of the pinhole diffraction pattern produced by pinhole 208 illuminates a second pinhole 210 with a diameter of 25 μm. These pinholes "clean" the beam 203 improving its spatial coherence and enhancing the quality of the hologram. All but the primary lobe of this second pinhole pattern is blocked by iris 212 where convex lens 214 then collimates the beam, which is brought to a focus by convex lens 216 at a point approximately 2 mm from the aerosol nozzle outlet 244. In an embodiment, the convex lens 214 may have a focal length of 300 mm and the convex lens 216 has a focal length of 30 mm.

The aerosol nozzle outlet 244 and the aerosol nozzle inlet 246 may form the delivery device 104 in FIG. 1. In this embodiment, a nozzle and suction tube are used to direct aerosol particles into the scattering volume area (region), however the present invention does not limit the delivery mechanism. FIG. 2(*a*) shows, in more detail, one embodiment of the region. In other embodiments, the delivery device 204 includes a free-flowing channel of aerosol or particles entrained in a microfluidic channel or flow.

The optical trigger device 106 in FIG. 1 may be implemented using the photomultiplier tubes 220 and 228 along with the diode laser beams 236 and 240. In an embodiment, the PMTs 220, 228 are a Hamamatsu Corp. Model No. H6780-02 and the diode laser beam 236 is a 635 nm wavelength laser beam. The beam from the laser 236 is focused using the convex lens 238 into the region where the particles 217 are delivered by delivery device 244.

The focused laser beam scatters from particles 217 in the region. The scattered waves are focused using a convex lens 234 and pass through an iris 232, a 635 nm line-filter 230 and then passes to photomultiplier tube 228 if the wavelength of the focused light is 635 nm. The diode laser 240 generates a 670 nm beam which is focused using convex lens 242 into the region where particles 217 are delivered. The focused laser beam scatters from particles 217 in the region. The scattered waves are focused using a convex lens 226 and pass through an iris 224, a 670 nm line-filter 222 and then to photomultiplier tube 220 if the wavelength of the focused light is 670 nm. The laser 202 may be pulsed only when both photomultipliers 220 and 228 detect light for their particular wavelength, at which point it is established that there is particle 217 in the region. The controller 247 uses a processor 239 to execute a FFT module 250 to generate the particle's image 254 from the hologram sensed by sensor 218. For instance, the sensor 218 may be spaced apart from the particle stream by a distance of approximately 8 cm in some cases. In an embodiment, the controller 247 identifies the particle by matching its holographic image with images stored in database 252 stored in memory of the controller 247. The database 252 may store a digital library of simulated or measured images. The resolution of the image produced by the controller 247 for this embodiment of the inline system is on the order of 5 µm, but may readily be improved to less than 5 µm by using a shorter wavelength laser 202 and a sensor 218 with smaller pixel dimensions.

Figure 2B:
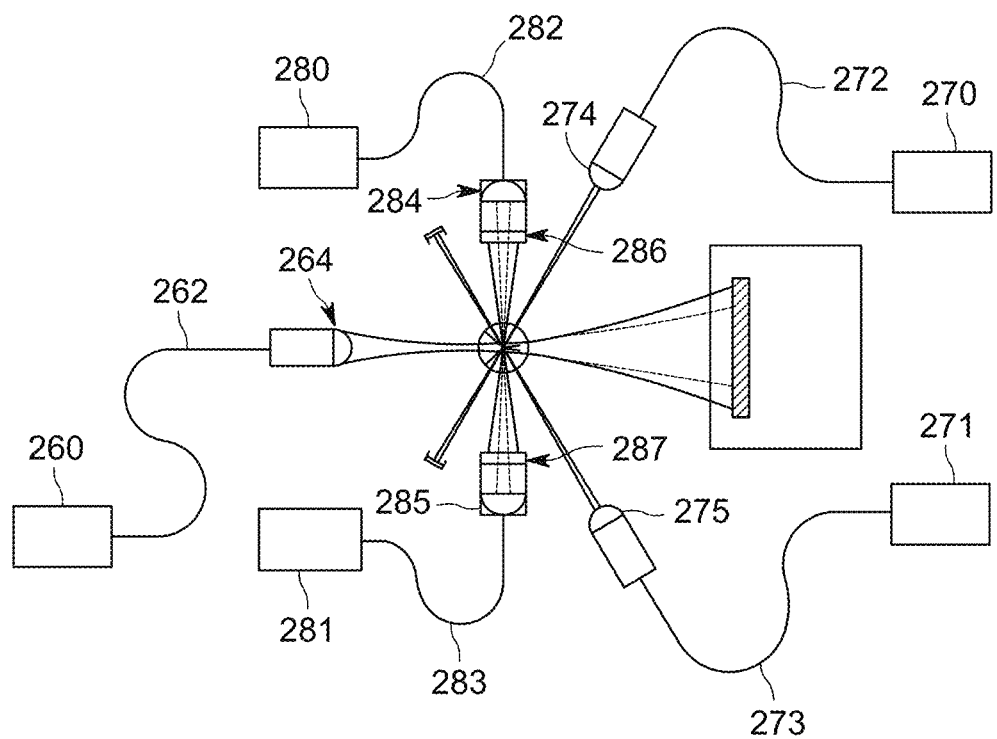

FIG. 2(b) illustrates another embodiment of implementation 200 using fiber optics instead of fixed laser 202. Here, a main laser 260 may be a triggerable, pulsed fiber laser (e.g., 400 nm range). Light from this pulsed fiber laser is conveyed to the "region" by an optical fiber 262 and an output lens 264 (such as an aspherical lens combination). The same focusing to form a virtual point source is performed and the particle is illuminated similarly as in implementation 200. The diode lasers 270, 271 for the PMT trigger system can also convey light to the region by optical fiber 272, 273 which is focused by to output lens 274, 275. The PMTs 280, 281 receive their light through optical fibers 282, 283. The coupling lens 284, 285 near the region are guarded by interference line filters 286, 287 that serve the same purpose as in the trigger system in FIG. 2. The incorporation of fiber optics can simplify the optical design, by making the device more compact and lighter. Using optical fibers may also eliminate the delicate alignment requirements of the optical elements. And, they can also make the system more durable and less vulnerable to mechanical shock.

Figure 2C:
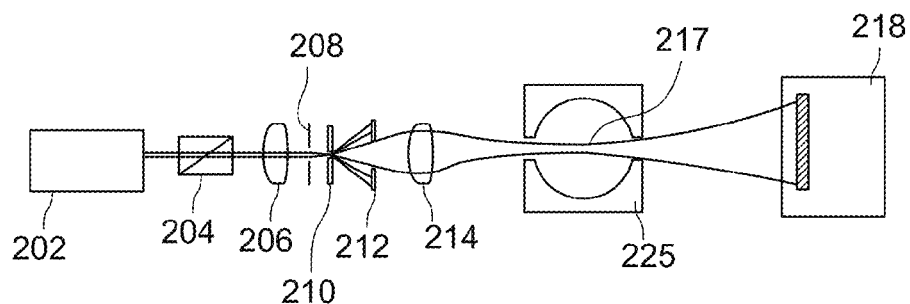

FIG. 2(c) illustrates yet another embodiment of implementation 200 of apparatus 100 of FIG. 1. The region may be defined by a particle trap 225, such as a spherical-void electrodynamic levitator (SVEL), which the beam from the laser 202 enters through a window thereof, and the scattered beam exits through a window thereof. For example, the particle trap 225 may have a spherical void (e.g., 25 mm dia.) used to confine particles and may include small holes (e.g., 6.3 mm dia.) to allow for the introduction of particles and optical access to the trapping region. An adjustable voltage may be applied to the particle trap to control particle flow and trapping for particle detection. Particles confined in the particle trap 225 are illuminated by light diverting from the collimated/focused beam of light, which effectively acts as a virtual point source producing a spherical wave. This diverging illumination wave continues to expand as it reaches the image sensor 218 along with the scattered light from the particle 217. The resulting interference pattern between these waves across the sensor is the hologram. By using a short-focal length lens to form a virtual source near the particle, the light illuminating the particle can be more intense than it would be if only a pinhole is used for illumination. This results in a relative amplification of the particle's scattered wave at the sensor, which may enhance the interference structure of the hologram leading to improved particle-image quality. If the virtual source is formed near the particle, there can be much more flexibility in "working distance" between the lens 214 and the aerosol particle stream. The working distance is based on the focal length of the lens 214, and may enable the working distance to be readily changed by changing the focal length of the lens 214. By contrast, in conventional detection apparatuses there is usually a pinhole or a microscope objective which must be spaced very close (e.g., <1 mm) to the sample. This spacing is inherent to the conventional apparatuses and thus is not readily changeable.

Figure 2D:
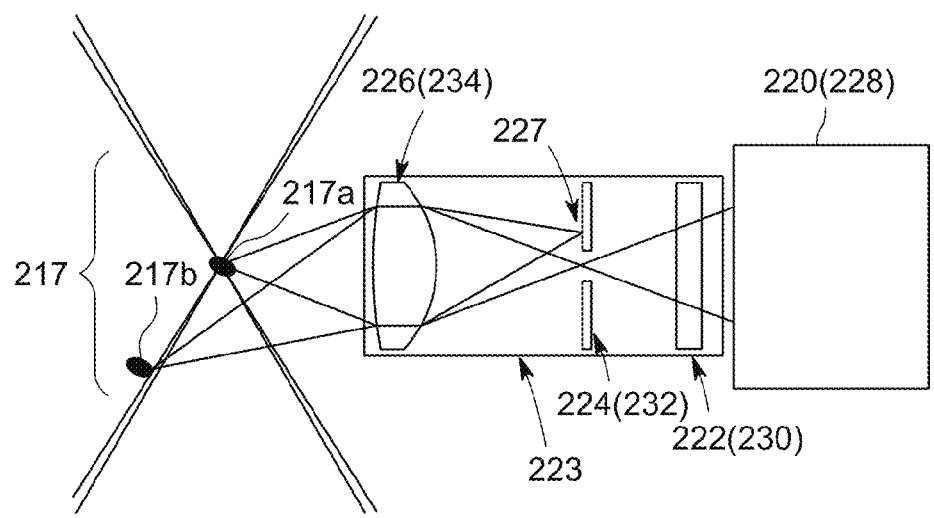

FIG. 2(d) illustrates one embodiment of the PMT sensing units of FIG. 2 in more detail. Here, the lens 226 (234) and the iris 224 (232) are used to spatially filter the scattered trigger light from the particles 217. If a particle 217a is in the desired location (e.g., the intersection of the trigger beams or the "region") then its light makes it to the PMT. If there is a stray particle 217b away from the desired location, its light 227 is blocked by the iris 224 (232). The light passing through the iris 224 (232) passes through line filter 222(230) onto the PMT 220 (228). The various elements may be housed in a lens tube 223 to prevent stray light from being detected. This arrangement may enhance the sensitivity of the trigger system to respond only to a particle in the trigger beam-intersection, especially when many particles are present in and around the region at the same time.

Figure 2E:
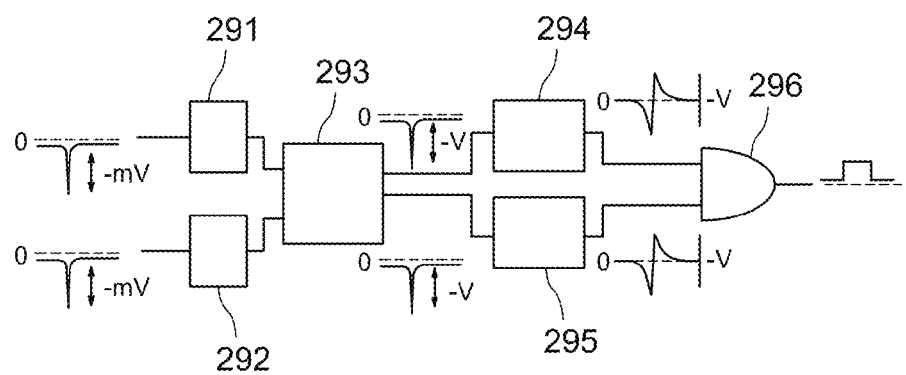
Figure 3:
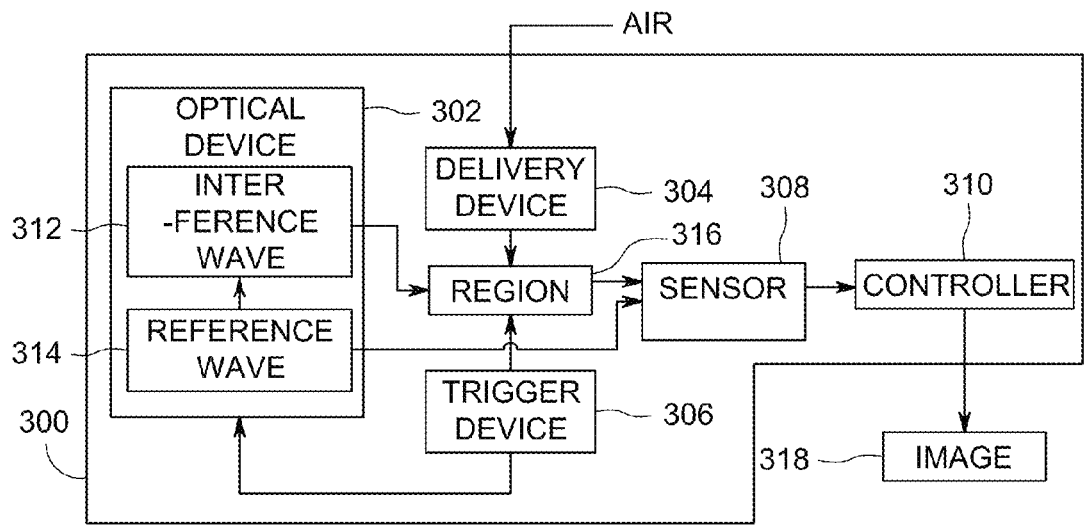
FIG. 3 is a functional block diagram of another apparatus for holographic imaging of aerosol particles in accordance with at least one embodiment of the present invention.

FIG. 2(e) illustrate one embodiment of the trigger system electronics for the optical trigger device 106 in FIG. 1. The output signals from the photomultipliers 220 and 228 may be amplified using amplifiers 291, 292, respectively. In some embodiments, amplifiers 291, 292 may be ORTEC Model 750 amplifiers. The output from amplifiers 291, 292 is then input to a quad analyzer 293 (e.g., an ORTEC Model 850) which in turn outputs two signals to processor 294, 295 (e.g., SRS analog processor). Output from the processors 294, 295 is input to logic unit 296 (e.g., an ORTEC Model CO4020 Logic Unit) which may be configured to perform the function of an AND gate circuit and output a signal to the laser 202. The signal may be a TTL signal, for instance.

In some embodiments, one or more of the NPBS 204, the pin hole 208, and the convex lens 216 illustrated in FIG. 2 may be omitted from implementation 200. This is because the polarizer and/or dual pin holes may only be needed, in some instances, if the light source (laser) has poor beam quality. In addition, other optical elements may be removed where they are considered redundant or superfluous.

Further using a pulsed light source may also permit investigation of particle systems in motion. Other elements in various embodiments may be the same or similar as those in implementation 200 shown in FIG. 2.

The light scattering pattern from an aerosol particle is generally a function of its size, shape, composition and/or surface structure. The light scattering pattern signal may be used to characterize the particle. In particular, the angular structure of a particle's scattering pattern may be related to the particle's overall shape through a Fourier-transform relationship. For example, information relating to the largest length of the particle is contained in the small angle region of the scattering pattern. Likewise, small length scale features of the particle, such as surface roughness, are generally contained in larger angle regions of the pattern. Consequently, holographic imaging of the particle's overall shape dictates that the hologram is formed from a portion of the particle's scattering pattern that includes the small forward scattering angles. However, because of the small size of the particles, it may be difficult to separate this small forward angle region of the pattern from the much more intense unscattered illumination beam. This problem may be overcome or ameliorated using a spatial filtering technique in which the unscattered light is removed from the pattern.

A digital hologram or interference image may include gray-scale image data which corresponds to the intensity distribution of interference of the incident and scattered waves across the image sensor. A nested ring appearance, which may be visible at some portions of the holographic image for a point-like particle, is due to the intersection of the spherical wave structure of the scattered wave with the planar incident wave.

To obtain images of a particle from the digital hologram, one or more pixels of the hologram may be regarded as a point electric-dipole with polarization proportional to the gray-value of the pixel. If a pixel in the hologram is black, indicating no light on that portion of the image sensor, then the polarization may be assumed to be zero. Conversely, for a white pixel value, the Maxwell volume integral equation may be used to calculate the electric field resulting from the radiation of the collection of dipoles corresponding to the hologram pixel. The magnitude and/or phase of this radiation, or reconstruction field is then calculated in a plane parallel to the hologram, but separated from it by a distance equal to the separation between the particle and the image sensor. This results in a two-dimensional computer-generated image of the particle in this place as given by the distribution of reconstruction-field magnitude. The phase, the magnitude, or both, of this field can be used to generate a three-dimensional rending of the particle.

One embodiment for generating an image of the sample aerosol particle according to the sensed interference pattern will now be described. Let the source of the reference wave, laser 202, be located at a distance "l" from the particle 217 and the sensor 218 at a distance d. Provided that kl and kd are large enough to satisfy far-field conditions described in M. Mishchenko, L. Travis, and A. Lacis, "Multiple scattering of light by particles: radiative transfer and coherent backscattering," Cambridge: Cambridge University Press, 2006, pp. 74-78, herein incorporated by reference in its entirety.

The reference and scattered waves will be transverse and spherical at the sensor 218 and can be represented entirely by their scattering amplitudes as described by M. Berg and G. Videen, "Digital holographic imaging of aerosol particles in flight," Journal of Quantitative Spectroscopy & Radiative Transfer 112 (2011) pp. 1776-1783, herein incorporated by reference in its entirety, as follows:

$$E^{ref}(r) = \frac{e^{ikr}}{r} E_1^{ref}(\hat{r}), E^{sca}(r) = \frac{e^{ikr}}{r} E_1^{sca}(\hat{r}) \quad (1)$$

respectively. Then, the intensity of the total wave across the sensor's face is:

$$I^{holo}(r) = \frac{c\varepsilon_0}{r^2} \left| E_1^{ref}(\hat{r}) + E_1^{sca}(\hat{r}) \right|^2, \quad (2)$$

where c and $\varepsilon_0$ are the vacuum speed of light and electric permittivity of free space, respectively. Expanding Eq. (2) gives:

$$I^{holo}(r) = \quad (3)$$
$$\frac{c\varepsilon_0}{r^2} \{ |E_1^{ref}(\hat{r})|^2 + |E_1^{sca}(\hat{r})|^2 + [E_1^{ref}(\hat{r})]^* E_1^{sca}(\hat{r}) + [E_1^{sca}(\hat{r})]^* E_1^{ref}(\hat{r}) \},$$

where the asterisk denotes complex conjugation. The quantity $$\frac{c\varepsilon_0}{r^2} |E_1^{ref}(\hat{r})|^2 = I^{ref}$$

in Eq. (3) is the intensity across the sensor 218 when no particle is present, and hence can be considered a known quantity (reference) measured before the introduction of an aerosol sample. Subtracting the reference intensity from Eq. (3) and dividing the remaining terms by the reference gives:

$$I^{con}(r) = \frac{I^{holo}(r) - I^{ref}(r)}{I^{ref}(r)} \quad (4)$$
$$= \frac{|E_1^{sca}(\hat{r})|^2}{|E_1^{ref}(\hat{r})|^2} + \frac{[E_1^{ref}(\hat{r})]^* E_1^{sca}(\hat{r}) + [E_1^{sca}(\hat{r})]^* E_1^{ref}(\hat{r})}{|E_1^{ref}(\hat{r})|^2},$$

Often, the intensity of the reference wave at the sensor 218 is much greater than that of the scattered wave. This is especially true in this work where the objects being illuminated are small particles, as opposed to the macroscopic sized objects involved in many other applications. This means that the term $$\frac{|E_1^{sca}(\hat{r})|^2}{|E_1^{ref}(\hat{r})|^2}$$

in Eq. (4) can be neglected, leaving:

$$I^{con}(r) \simeq \frac{[E_1^{ref}(\hat{r})]^* E_1^{sca}(\hat{r}) + [E_1^{sca}(\hat{r})]^* E_1^{ref}(\hat{r})}{|E_1^{ref}(\hat{r})|^2} \quad (5)$$

This intensity pattern, which is the difference between two measurements, with and without the particle 217 present, is known as a contrast hologram. The key characteristic of $I^{con}$ is its linear dependence on the amplitude of the particle's scattered wave. This means that the phase of the scattered wave over the detector is encoded in the measurement. Consequently, the interference pattern can be used to reconstruct unambiguously an image of the particle that closely resembles that obtained from conventional microscopy. The contrast hologram is envisioned as a transmission diffraction-grating illuminated by a normally incident plane wave, i.e., a reconstruction wave. In an embodiment, the Fresnel-Kirchhoff approximation is then used to describe the light diffracted from this grating in a parallel plane separated by a distance z from the grating along the z-axis. If z corresponds to the distance between the particle and sensor 218 during the hologram measurement (z=d) the resulting diffraction pattern in this so-called reconstruction plane yields an image 254 of the particle 217. The image 254 may be essentially equivalent to a conventional microscope image of the particle 217.

One advantage of using the Fresnel-Kirchhoff approximation to generate the reconstructed particle image is that the approximation's mathematical form is essentially a discrete Fourier transform of the sensor 218 pixel values constituting $I^{con}$. This enables the use of the fast Fourier transform (FFT) in the calculation, thus substantially reducing the computation time required to render the particle image. In practice, d may not be known to sufficient accuracy to be able to reconstruct an image from a single application of the reconstruction routine. This inaccuracy is due to the variation in particle positions in the aerosol stream as they enter the region 105. Consequently, the image-reconstruction stage includes a focusing-like procedure: First an initial image is reconstructed using an estimate of d based on the experimental layout. Then, the reconstruction plane is scanned along the z-axis in small steps until the reconstructed image comes into focus.

In other embodiments, the reconstruction of the holographic image may use a computational procedure using a Kirchoff-Helmholtz formula, such as Equations 2 and 3 of U.S. Pat. No. 6,411,406 entitled "Holographic Microscope and Method of Hologram Reconstruction," herein incorporated by reference in its entirety.

By using the disclosed holographic techniques, multiple particles may be in the scattering region at a time. In addition, the holographic techniques do not require particles to be in each other's far-field zones. Thus, if multiple particles are present when the hologram is recorded, they can be independently imaged digitally from the hologram by varying the distance from the hologram to the reconstruction plane. Accordingly, it is possible to digitally target or "focus-in" on one particle or another.

Holographic images that can be used to characterize the morphology of particles may be on the order of the wavelength of the illuminating light, which may be between 4 and 7 μm in size and larger for visible light, and resolutions may be obtained approximately 1/10 of this wavelength, for example, in some implementations.

FIG. 3 is a functional block diagram of another apparatus 300 for holographic imaging of aerosol particles in accordance with at least one embodiment of the present invention. Apparatus 300 comprises an optical device 302, a delivery device 304, a trigger device 306, a sensor 308 and a controller 310. The optical device 302 generates a particle-illuminating wave 312 and a reference wave 314. The particle-illuminating wave 312 is routed through the region 316. The delivery device 304 delivers particles from the air in the surrounding environment into region 316, and the particle-illuminating wave 312 scatters when it hits the particles in the region 316. The reference wave 314 from the optical device 302 is not sent through the region 316, thus it is un-scattered by particles in the region 316. The combination of the particle-illuminating wave 312 with the reference wave 314 results in interference of the two waves producing an interference pattern, i.e., the hologram, which is captured by sensor 308. The sensor 308 couples the sensed hologram to controller 310. In an embodiment, the controller 310 performs a Fast Fourier transform on the hologram to generate an image 318 of the particles.

FIG. 4 is a functional implementation 400 of the apparatus 300 in accordance with one of the embodiments of the present invention. Apparatus 400 includes an optical device 402, a trigger system 404, a sensor 406 and a processor 408. A delivery device is not shown in this figure, but may be similar to delivery device 244 and 246 shown in FIGS. 2 and 2(*a*). In an embodiment, the optical device 402 comprises a light source 412 (e.g., a 70 ns pulsed Nd:YAG laser, e.g., Spectra Physics Lasers, Inc., model Y70-532Q, frequency doubled to 532 nm), a non-polarizing cube beam splitter (NPBS) 414, an angled mirror 416 a concave expanding lens 418, a convex collimating lens 420, a convex collimating lens 422, a mirror 424 with a small through-hole 425, a second NPBS 426, a convex focusing lens 428, iris 429, and a convex collimating lens 430. When the length of the pulse is very short, the motion of the particle during this time may be assumed to be negligible such that the particle may be considered "frozen" in space.

The detecting device 404 comprises two diode lasers 432 and 436, respectively emitting 635 nm and 670 nm light in an embodiment. The beams emitted from the diode lasers 432 and 436 intersect where a particle 401 will be delivered and scatter the respective wavelength light to be detected by photomultipliers 434 and 438. The detecting device 404 may further include additional elements (not shown) similar to those shown in FIG. 2, such as convex lens 238 and 242 for focusing the laser beams emitted from the diode lasers 432, 434 onto the particle 401, convex lens 226, 234 for focusing the scattered light from the particle 401 toward the PMTs 434, 438, and filters 222, 230 for selectively filtering a particular wavelength of light that is received by the PMTs 434, 438. When the PMTs 434 and 438 detect a particle 401, the optical device 402 is enabled and the laser light source pulses laser beam 403.

The NPBS 414 splits the laser beam 403 into two beams 413 and 417. Beam 413 interacts with particle 401 causing a first scattering pattern, in addition to non-scattered light, to emerge at lens 422. The lens 422 serves two purposes. First, the lens 422 is placed at a distance of one focal length from the scattering volume where particle 401 is located, such that the scattered light is collimated when it leaves lens 422. Second, the un-scattered illuminating beam is brought to a focus at the back focal plane of lens 422. Since it is desired to remove this portion of un-scattered light, the mirror 424 reflects the scattered light and the un-scattered illuminated focused beam passes through through-hole 425 of the mirror 424. In some embodiments, the mirror 424 can be configured to separate the scattered and unscattered light down to very small angles i.e., 0.1 degree from the forward direction. The scattered light is then reflected to NPBS 426. It will be appreciated that other optical elements might also be used to separate the scattered light from the unscattered light. This separation also removes the D.C. or so-called "zero order" region in the hologram, which is the high-intensity region due to the unscattered light.

The second split wave 417 from NPBS 414 serves as a reference beam and is deflected towards the mirror 416, which may be placed at an angle (e.g., a 45 degree angle) in an embodiment, further deflecting the beam. In some embodiments, a neutral density (ND) filter 415 may be provided to maximize the contrast of the interference fringes by making the field intensity of the reference beam 417 approximately the same as that of the scattered light field. The lens 418 expands the beam 417 and the convex lens 420 collimates the light from lens 418 onto the NPBS 426. The NPBS 426 then combines the reference beam 417 with the particle scattered wave reflected from mirror 424 into combined interference light. The NPBS 426 may be placed on a rotation stage, introducing a small offset angle between the reference wave and the collimated scattered wave (not shown). This introduces a small angular separation between the so-called "twin images" that occur during the image reconstruction stage. Convex lenses 428 and 430 image the interference pattern of the reference wave and the collimated wave through the iris 429 onto the sensor 406. The lens pair 428, 230 and the iris 429 in front of the sensor 406 are used to suppress stray light from dust and the like that collects on the optical surfaces between the region and the sensor 406. In an embodiment, the sensor 406 is a Charged Coupled Device (CCD) camera, but in other embodiments, the sensor 406 may be any sensor capable of capturing an image such as an Intensified Charged Coupled Device (ICCD) camera or Complementary Metal-Oxide-Semiconductor (CMOS) camera, and the like. In an embodiment, a Finger Lakes Instrumentation, LLC Model ML8300 CCD having a pixel size of approximately 5.4 μm may be used. The sensor 406 outputs the interference pattern to the computer system 408, containing a processor 440 and memory 442 with a FFT 444 and a database 446. The processor executes the FFT and generates an image 410 of the particles. The resolution of the holographic image 410 produced by the system 408 for a dual-beam system is, in this embodiment, on the order of about 1 micron.

Figure 4:
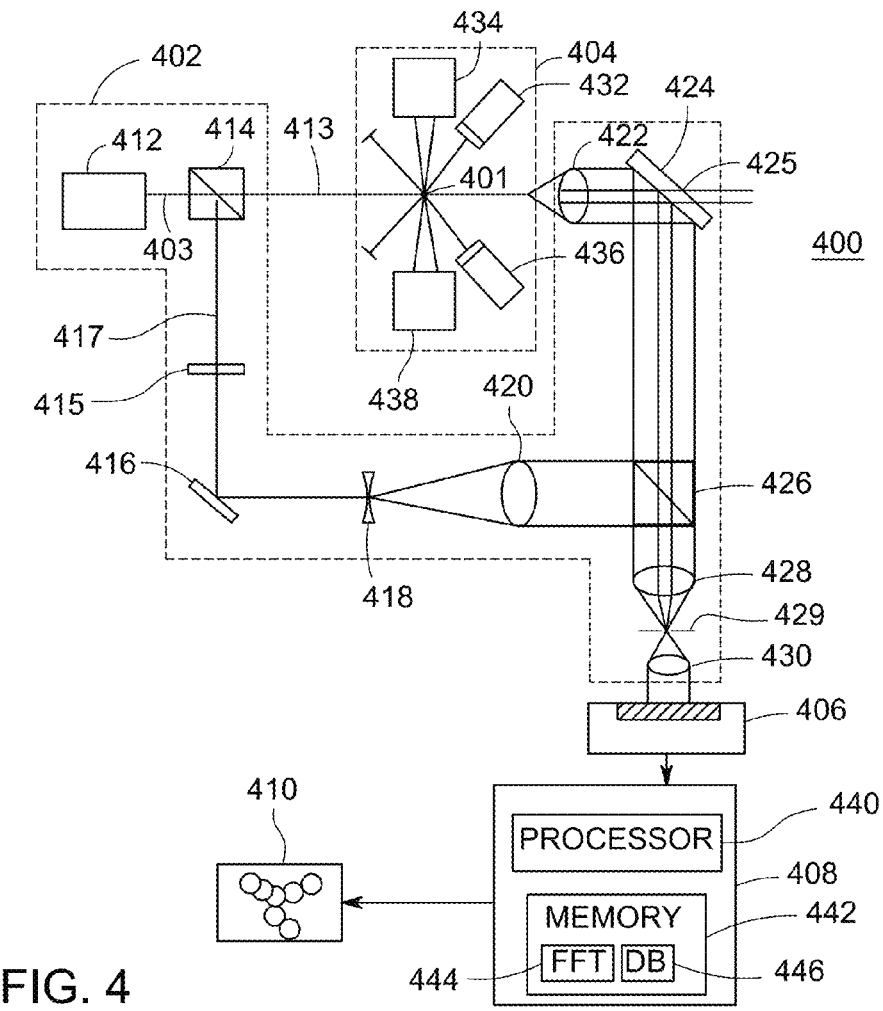
FIGS. 4 and 4(a)-4(b) are functional implementations of the apparatus in FIG. 3 in accordance with one of the embodiments of the present invention.
Figure 4A:
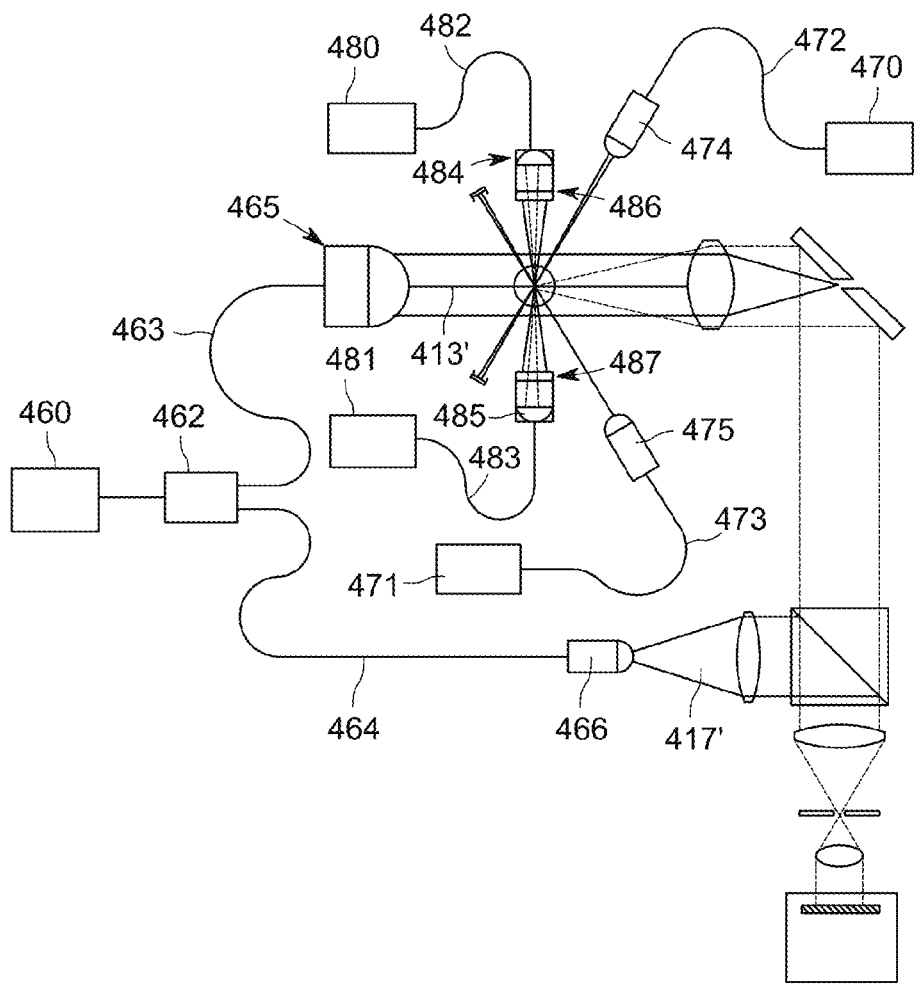

FIG. 4(a) illustrates another embodiment of implementation 400 of FIG. 4 partially implemented with fiber optics. Here, a main laser 460 may be a triggerable, pulsed fiber laser (e.g., 400 nm range). The neutral density filter 415 in FIG. 4 may be replaced by the variable coupler 462 that can be used to change the proportion of fiber-laser-light from the pulsed fiber laser 460 that is split between the two optical fibers 463, 464 that go off to collimators 465, 466 for conveying beams 413', 417'. The collimators 465, 466 may include aspherical lenses, in some instances. The same focusing to form a virtual point source is performed and the particle is illuminated as in implementation 400. The diode lasers 470, 471 for the PMT trigger system can also convey light to the region by optical fiber 472, 473 which is focused by to output lens 474, 475. The PMTs 480, 481 now receive their light through optical fibers 482, 483. The coupling lens 484, 485 near the region are guarded by interference line filters 487, 488 that serve the same purpose as in the trigger system in FIG. 4.

Figure 4B:
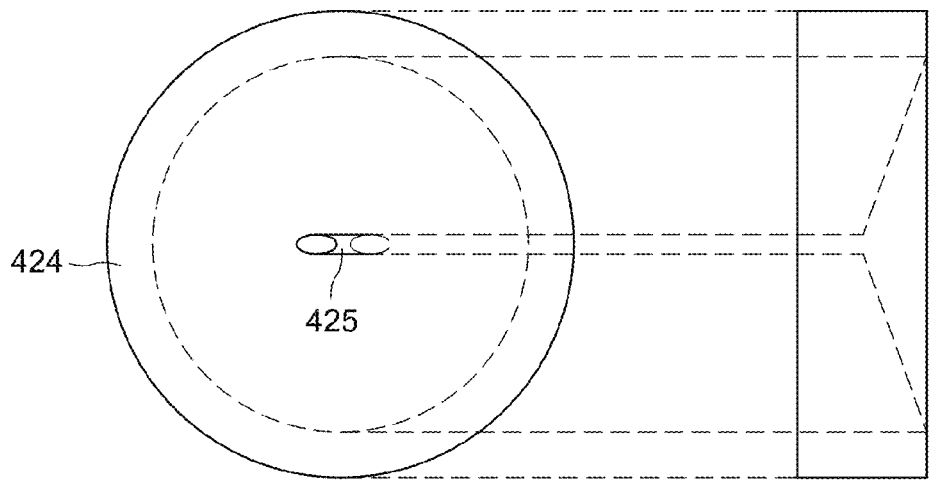

FIG. 4(b) illustrates one embodiment of mirror 424 in more detail. The through-hole mirror is configured to separate small angle scattered light and remove any direct current (DC) terms in the holographic image. The through-hole 425 can be formed by drilling an angled hole with respect to the mirror-surface normal direction, for example. Here, the angled hole is shown at 45 degrees.

Other elements of implementation 400 may be the same or similar as those of implementations 200 in some embodiments, such as, for example, optical elements/systems for focusing or collimating light, trigger system electronics and a particle trap.

By using two separate beams, it may be further possible to modify the intensity of the reference beam, the incident beam, or both, to increase the contrast of the fringes on the sensor 406. And, with this configuration, the particle's forward scattered light can be collected over an angular range of about 0.1 to 20 degrees in the polar angle and 0 to 360 in the azimuthal angle. The interference pattern recorded by the sensor 406 may be a digital off-axis hologram. From this hologram, an image, e.g., a three-dimensional image of the particle, can be reconstructed computationally. Holograms can be recorded for one or more particles in the aerosol sample as they flow through the scattering volume substantially in real-time. The scattered field remains stable with the particle located at different positions within the scattering volume.

Limitations on the apparatus may be the read-out (or refresh rate) of the image sensor, the size of the image sensor, and/or the processing speed of the image processor for digital reconstruction. Features in the interference pattern at the image sensor plane that are finer than the pixel size may be averaged out across that pixel, although, this may result is some image loss, in some instances. The finite size of the image sensor can also limit the resolution with the resolution of the reconstructed image being diffracted limited by the array pixels. Assuming a pixel size of 5.4 micrometers and an image sensor array size of 3000×3000 pixels, reconstruction resolution of image features with length scaled less than one micron may not be feasible in some instances.

In addition to pixel size, there may also be a restriction on the maximum particle size that may be feasible for imaging. This limitation may originate from the requirement that the collimated scatting wave and the incident reference wave intersect at the image sensor plane at an angle large enough to separate the particle image from the so-called "zero order" term. This term represents a region in the reconstruction plane around the forward direction where the autocorrelation of the particle's image forms than its image alone. For example, one typical upper size-limit for 532 nm illuminating light may be about 20 micrometers. This may not be a critical limitation for all monitoring situations, since particles of interest tend to be smaller than 10 micrometers and larger particles tend to fall out of the atmosphere more rapidly.

Figure 5:
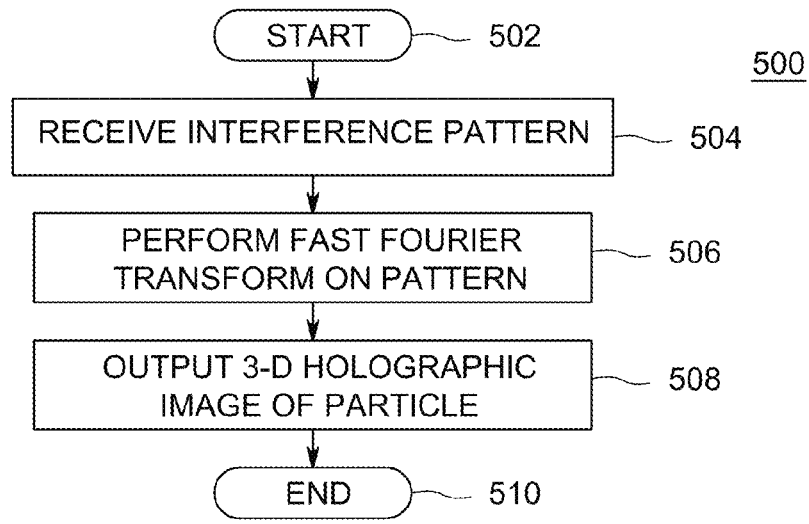
FIG. 5 is a flow diagram of a method of performing holographic imaging of aerosol particles in accordance with embodiments of the present invention.

FIG. 5 is a flow diagram of a function 500 for holographic imaging of aerosol particles in accordance with embodiments of the present invention. The method 500 is an implementation of execution of the FFT module 250 executed by the processor 249 in memory 248. The method 500 begins at step 502 and proceeds to step 504. At step 504, the interference pattern of the scattered light wave and the un-scattered wave, i.e., the hologram, is received from the sensor 218. The processor 246 then performs the Fast-Fourier transform on the interference pattern at step 506. The method then outputs an image 254 of the particles 217 at step 508. The method ends at step 510.

Figure 6:
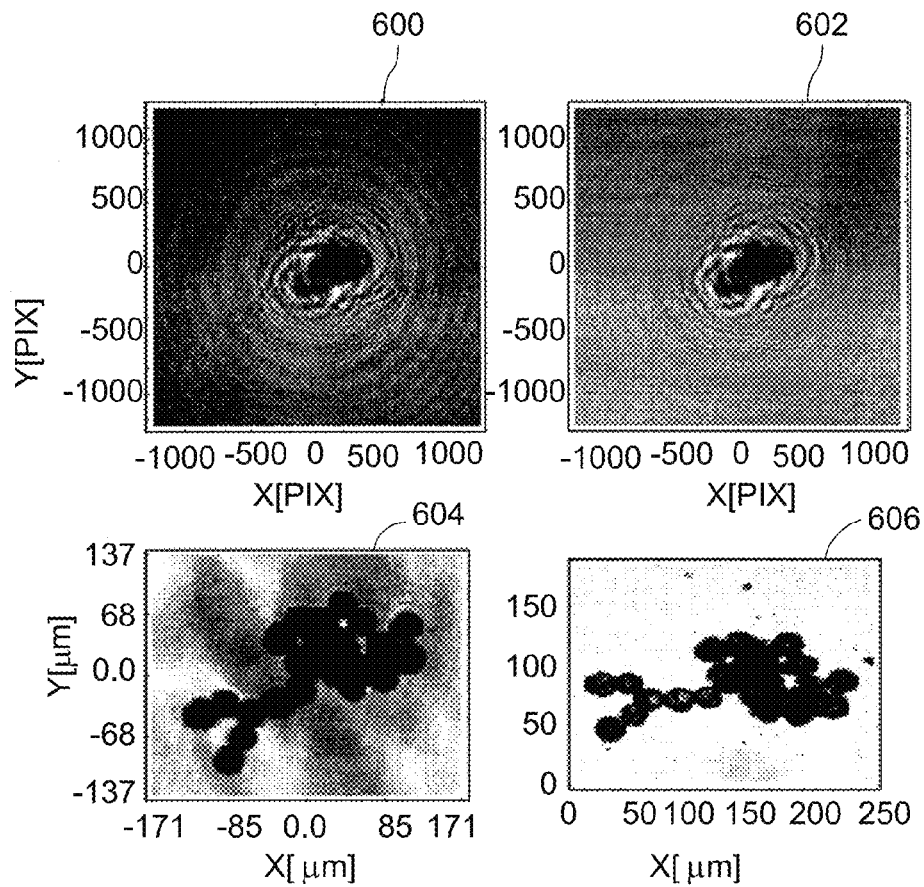
FIG. 6 is an illustration of interference patterns as detected by the apparatuses above and microscopic images imaged by a regular microscope of a cluster of ragweed pollen particles.

FIG. 6 is an illustration of the holograms and microscope images of a cluster of ragweed pollen particles. Image 600 is a hologram for the ragweed pollen particle produced by sensor 218 according to an embodiment of the present invention. Image 602 is a further-filtered hologram $I^{con}$ produced by the sensor 218 and described above. The method 500 is then applied to image 602 to produce an image 604 of the ragweed pollen particles. Rings surrounding the images may be out of focus images which are artifacts of the in-line implementation 200. This may also be the case for implementation 400. Although, if a small angle separation is deliberately interposed between the scattered and the reference wave images (for instance, using a rotating stage, as discussed above) then unwanted artifacts may be separated from the real image, such as during reconstruction.

Finally, image 606 is a depiction of a conventional microscope image of the same cluster of ragweed pollen particles, for comparative purposes.

Figure 7:
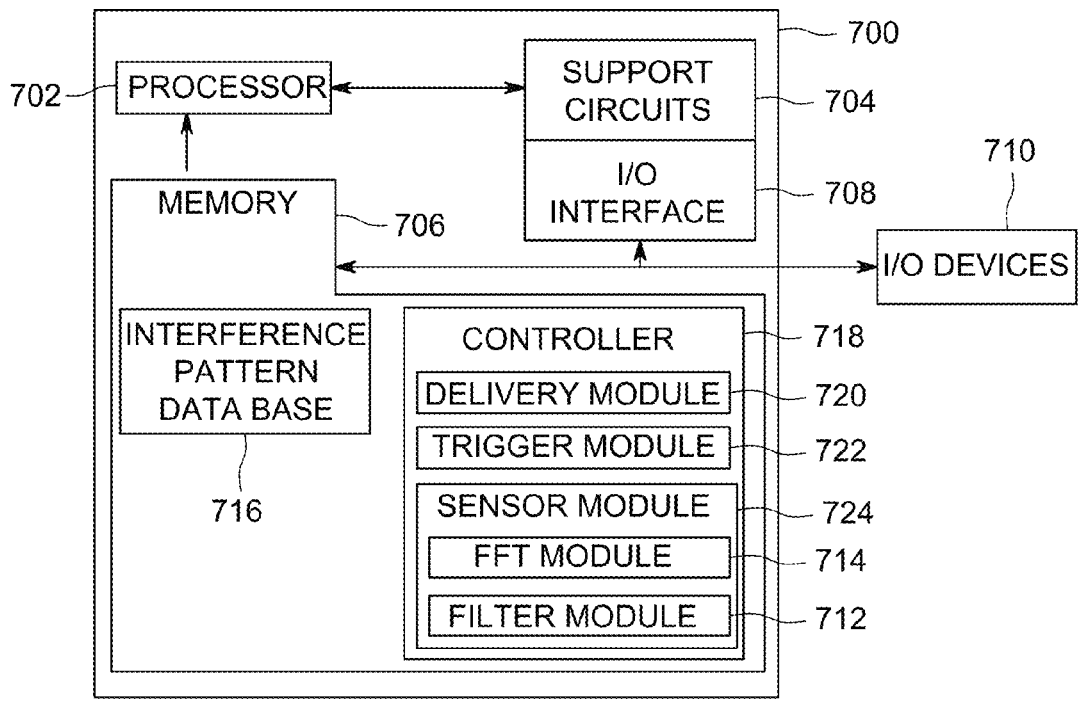
FIG. 7 is a block diagram of an embodiment of a computer system in accordance with one or more aspects of the present invention.
Figure 8:
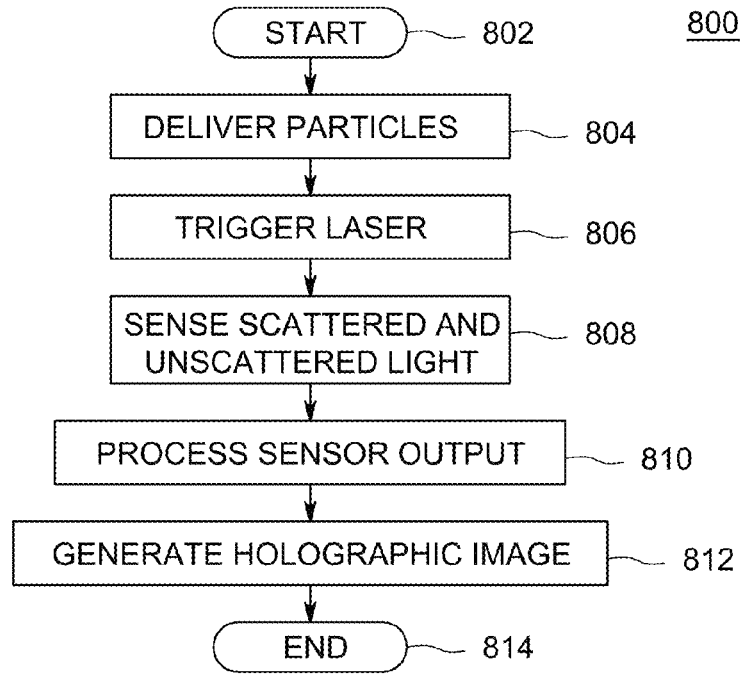
FIG. 8 is a flow diagram of a method for holographic imaging of aerosol particles in accordance with embodiments of the present invention.

By comparing these images, one can see that the holographic apparatus successfully produces an accurate image of the pollen cluster, with sufficient resolution to discern individual pollen particles and even a faint signature of the single-particle surface roughness seen in the microscope images. This corresponds to a resolution roughly between 8-10 μm, although a more rigorous resolution analysis is not performed. Referring to the measured and contrast holograms shown in this figure, it is apparent how subtraction of the incident beam across the CCD, i.e., $I^{ref}$ removes noise due to imperfections in the incident beam profile. This has the consequence of producing a "cleaner" contrast hologram, which subsequently improves the particle image. The holographic and microscope images of the cluster may differ slightly in overall size and detailed structural form. Although it is clearly the same cluster in (c) and (d), the differences are likely due to shifting of the cluster on the microscope slide during transfer from the apparatus to the microscope. FIG. 7 is a block diagram of an embodiment of a computer system 700 in accordance with one or more aspects of the present invention. The computer system 700 may be used to implement a portion of any one of the apparatuses 100, 200, 300 and 400 for holographic imaging of aerosol particles. The computer system 700 includes a processor 702, various support circuits 704, and memory 706. The processor 702 may include one or more microprocessors known in the art. The support circuits 704 for the processor 702 include conventional cache, power supplies, clock circuits, data registers, I/O devices 710, and the like. An input/output (I/O) interface 708 may be directly coupled to the memory 706 or coupled through the supporting circuits 704. The I/O interface 708 may also be configured for communication with input devices and/or output devices 710, such as, network devices, various storage devices, mouse, keyboard, display, and the like.

The memory 706, or computer readable medium, stores non-transient processor-executable instructions and/or data that may be executed by and/or used by the processor 702. These processor-executable instructions may comprise firmware, software, and the like, or some combination thereof. Modules having processor-executable instructions that are stored in the memory 706 comprise controller module 718 and an interference pattern database 716. The controller module 718 comprises a delivery module 720, a trigger module 722 and a sensor module 724 which comprises a Fast Fourier Transform module 714 and a filter module 712. The delivery module 720 controls the delivery device 304 to deliver aerosol particles into region 316. The controller 718 detects when the trigger module 722 senses a particle in region 316 and enables optical device 302. The controller 118 then enables sensor 308 to sense the scattered and un-scattered wave interference pattern. The sensor module 724 executes the filter module to perform background subtraction on the sensed image to generate $I^{con}$ and executes the FFT module 714 to produce an image from $I^{con}$. The system 700 then identifies the hologram and/or the image produced with stored images in the database 716. The memory 706 may include one or more of the following random access memory, read only memory, magneto-resistive read/write memory, optical read/write memory, cache memory, magnetic read/write memory, and the like, as well as signal-bearing media, excluding non-transitory signals such as carrier waves and the like.

FIG. 8 is a flow diagram of a function 800 for holographic imaging of aerosol particles in accordance with embodiments of the present invention. The method 800 is an implementation of execution of the controller 718 executed by the processor 702 in memory 706. The method 800 begins at step 802 and proceeds to step 804, where the particles are delivered into a region by the delivery module 720. At step 806, the trigger module enables the optical device 302 to generate a particle-illuminating wave and a reference wave (unscattered). When the particle-illuminating wave interacts with aerosol particles, a scattered wave is generated. At step 808, the sensor module 724 senses the interference pattern between the scattered wave and the un-scattered wave, where the interference pattern is the hologram. At step 810, the sensor output is processed by filter module 712, to background subtract the sensed hologram. At step 812, the FFT module 714 is executed to generate an image of the particles 318. The method ends at step 814.

The apparatuses and methods disclosed herein may further be used in conjunction with other technologies, such as fluorescence, Raman spectroscopy, Laser-induced breakdown spectroscopy (LIBS) in a detector to additionally characterize particles.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

Various elements, devices, modules and circuits are described above in associated with their respective functions. These elements, devices, modules and circuits are considered means for performing their respective functions as described herein.

While the foregoing is directed to embodiments of the present invention, other and further embodiments of the invention may be devised without departing from the basic scope thereof, and the scope thereof is determined by the claims that follow.

The invention claimed is:

1. An apparatus for holographic imaging of an aerosol particle comprising:

- a delivery device configured to generate a flow of air to deliver the particle to and from a region;
- a particle trap configured to trap and hold the particle in said flow of air substantially motionless in the region, and to later release the particle from said particle trap into said flow of air;
- a light source for outputting a first beam of light and a second beam of light, wherein the first beam travels into the region producing a first light wave which is un-scattered by the trapped particle and a second light wave that is scattered by the trapped particle, and the second beam does not travel into the region;
- a beam splitter for combining the second beam with the scattered light of the first beam into combined interference light;
- an image sensor for sensing an interference pattern created by the combined interference light; and
- an image processor configured to generate an image of the aerosol particle based on the sensed interference pattern.

2. The apparatus of claim 1 further comprising:

- a first optical system having at least one lens for focusing the first beam into the region.

3. The apparatus of claim 1 further comprising an optical trigger device for detecting the aerosol particles in the region comprising:

- a first diode laser beam and a second diode laser beam arranged in a crossed-beam configuration; and
- a first photomultiplier tube for detecting incidence of the first diode laser beam when scattered by the aerosol particles and a second photomultiplier tube for detecting incidence of the second diode laser beam when scattered by the aerosol particles,
- where the first light wave and the second light wave intersect in the region and where the light source is pulsed when the first and second photomultiplier tube detect incidence simultaneously.

4. The apparatus of claim 3 wherein the first diode laser beam and the second diode laser beam are of differing wavelengths and the first photomultiplier tube detects light with a first wavelength equal to a wavelength of the first diode laser beam and the second photomultiplier tube detects light with a second wavelength equal to a wavelength of the second diode laser beam.

5. The apparatus of claim 4, wherein the image sensor is activated when the optical device is pulsed, and the light source is a pulsed laser light source.

6. The apparatus of claim 1, further comprising: a beam splitter for splitting a beam of light from the light source into the first beam and the second beam.

7. The apparatus of claim 1, wherein the light source comprises a fiber laser for generating a beam of light and a coupler optically connected to the fiber laser for splitting the beam of light into the first beam and the second beam along distinct optical fibers.

8. The apparatus of claim 1, wherein the beam splitter is positioned on a rotation stage so as to introduce an angular offset between the combined interference light and the second beam.

9. The apparatus of claim 1, further comprising a second optical system having:
a mirror for reflecting the second beam; and
at least one lens for focusing the second beam.

10. The apparatus of claim 1, further comprising a third optical system having at least one lens for focusing the combined interference light onto the image sensor.

11. The apparatus of claim 1, further comprising:
a mirror for separating the scattered light from the un-scattered light, the mirror having a through-hole for allowing the un-scattered light to pass there through; and
a reflecting surface for deflecting the scattered light.

12. The apparatus of claim 1 wherein the image processor is configured to execute a Fast-Fourier transform to transform the sensed interference pattern into the image of the aerosol particle.

13. The apparatus of claim 1 wherein the image processor is configured to: (i) identify the particle based on the image by searching images in a digital database, (ii) construct a three-dimensional rendering of the particles using the phase, magnitude, or both, of an electric field associated with one or more pixels of the sensed pattern, or both.

14. The apparatus of claim 1, further comprising:
a filter for changing the field intensity of the second beam.

15. A method for holographic imaging of an aerosol particle comprising:
generating a flow of air to deliver the particle to and from a region;
trapping and holding the particle in said flow of air substantially motionless in the region using a particle trap and later releasing the particle from said particle trap into said flow of air;
outputting a first beam of light and a second beam of light, wherein the first beam travels into the region producing a first light wave which is un-scattered by the trapped particle and a second light wave that is scattered by the trapped particle, and the second beam does not travel into the region;
separating the scattered light from the un-scattered light of the first beam;
combining the second beam with the scattered light of the first beam into combined interference light;
sensing the interference pattern of the combined interference light; and
generating an image of the aerosol particle based on the sensed interference pattern.

16. The method of claim 15, further comprising:
introducing an angular offset between the combined interference light and the second beam.

17. The method of claim 15, wherein generating the image comprises:
constructing a three-dimensional rendering of the particles using the phase, magnitude, or both, of an electric field associated with one or more pixels of the sensed interference pattern.

18. The method of claim 15, further comprising:
modifying the field intensity of the first beam, the second beam, or both, such that the second beam is approximately the same intensity as that of the scattered light.

19. The method of claim 15 wherein generating the image comprises:
executing a Fast-Fourier transform to transform the sensed interference pattern into the image of the aerosol particle.

20. The apparatus of claim 1, further comprising a nozzle and suction device configured to generate said flow of air.

21. The method of claim 15, further comprises:
detecting the particle size, shape, or both.

22. An apparatus for holographic imaging of an aerosol particle comprising:
a delivery device configured to generate a flow of air to deliver the particle to and from a region;
a particle trap configured to trap and hold the particle in said flow of air substantially motionless in the region, and to later release the particle from said particle trap into said flow of air;
a light source for outputting a beam of light which travels into the region producing a first light wave which is un-scattered by the trapped particle and a second light wave that is scattered by the trapped particle;
an image sensor configured to sense an interference pattern created by interference between the first light wave and the second light wave; and
an image processor configured to generate an image of the aerosol particle based on the sensed interference pattern.

23. The method of claim 15, comprising trapping and holding multiple particles in the region, and generating individual images of the multiple trapped aerosol particles.

24. The method of claim 15, comprising generating multiple images of a single trapped particle.

* * * * *